United States Patent
Lee et al.

(10) Patent No.: US 6,876,497 B2
(45) Date of Patent: Apr. 5, 2005

(54) COLOR-SIMULATING APPARATUS

(75) Inventors: Den Hua Lee, 4F-15, No. 126, Sheng-Li Rd., Hsinchu (TW); Chi Luen Wang, No. 18, Lane 349, Sec. 2, Tung-Ta Rd., Hsinchu (TW); Chun Chien Hong, 14F, No. 60, Nan-Chang St., Taichung (TW)

(73) Assignees: Den Hua Lee, Hsinchu (TW); Chi Luen Wang, Hsinchu (TW); Chun Chien Hong, Taichung (TW); Mao-Sheng Chen, Kaohsiung (TW)

( * ) Notice: Subject to any disclaimer, the term of this patent is extended or adjusted under 35 U.S.C. 154(b) by 995 days.

(21) Appl. No.: 09/754,374

(22) Filed: Jan. 5, 2001

(65) Prior Publication Data

US 2001/0007505 A1 Jul. 12, 2001

(30) Foreign Application Priority Data

Jan. 7, 2000 (TW) .................................... 89200278 U

(51) Int. Cl.[7] ..................... G02B 21/14; G01N 21/25; G01J 3/50; G03B 21/26; F21V 9/00

(52) U.S. Cl. ..................... 359/634; 356/416; 356/420; 250/226; 353/28; 362/231

(58) Field of Search ..................... 250/226; 345/207; 353/28; 356/407, 416, 420; 359/634; 362/231

(56) References Cited

U.S. PATENT DOCUMENTS

| | | | | | |
|---|---|---|---|---|---|
| 3,867,039 | A | * | 2/1975 | Nelson | 356/407 |
| 4,310,314 | A | * | 1/1982 | Worn et al. | 434/101 |
| 4,685,808 | A | * | 8/1987 | Nakazawa et al. | 356/416 |
| 4,917,495 | A | * | 4/1990 | Steenhoek | 356/328 |
| 5,082,529 | A | * | 1/1992 | Burk | 162/198 |
| 5,468,645 | A | * | 11/1995 | Kirollos et al. | 436/164 |
| 6,369,893 | B1 | * | 4/2002 | Christel et al. | 356/417 |

* cited by examiner

Primary Examiner—David N. Spector
(74) Attorney, Agent, or Firm—Birch, Stewart, Kolasch & Birch, LLP

(57) ABSTRACT

A color-simulating apparatus is provided, which can be applied to change the color of an article to various colors. The color-simulating device first analyzes a color to be simulated and then produces a light having the color according to the analysis result. Lastly, the color light is used to provide the color of an article.

11 Claims, 4 Drawing Sheets

COLOR-SIMULATING APPARATUS

BACKGROUND OF THE INVENTION

1. Field of the Invention

The present invention relates to a color-simulating apparatus.

2. Description of the Related Art

Human beings living in the world are sensitive to the variation of colors. Various colors might affect the feeling of people. Therefore, sometimes people have to change the color of an article in order to arrange various colors in pairs. There are some prior arts focusing their research on colors and how to arrange various colors in groups. Conventionally, in order to change the color of an article, pigment or dye in various colors has to be coated on the article. This conventional method is troublesome and can not change the color of an article in real time.

Besides the conventional method described above, some prior-art articles are made of the material which can change its color under various temperatures or while illuminated by various intensities of lights. However, such an article can only change its color from deep to light or between two different colors. The color variation of the prior-art article is monotonous.

SUMMARY OF THE INVENTION

Accordingly, in order to overcome the drawbacks of the prior arts, an object of the present invention is to provide a color-simulating apparatus, which can be applied to change the color of an article to various colors.

Another object of the present invention is to provide a color-simulating apparatus, which can change the color of an article in real time.

According to this invention, the color-simulating apparatus first analyzes a color to be simulated and then produces a light having the color according to the analysis result. Lastly, the color light is used to provide the color of an article.

BRIEF DESCRIPTION OF THE DRAWINGS

The present invention can be more fully understood by reading the subsequent detailed description in conjunction with the examples and references made to the accompanying drawings, wherein.

DETAILED DESCRIPTION OF THE PREFERRED EMBODIMENT

Figure 1:
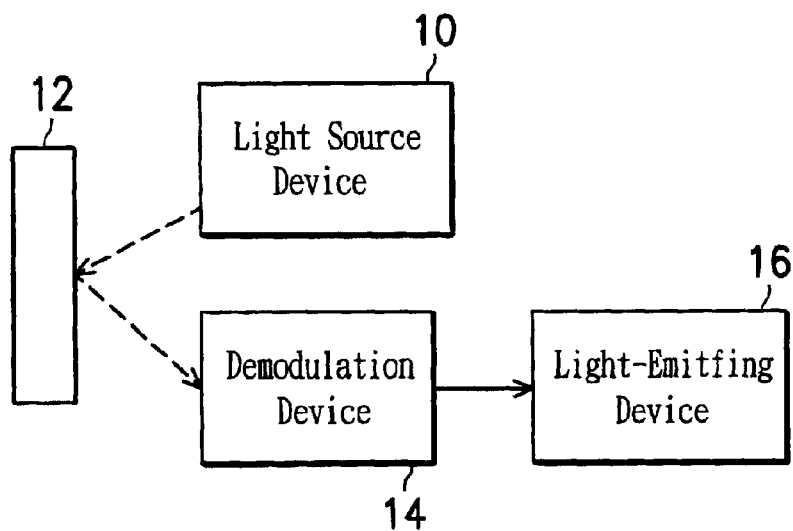
FIG. 1 is a diagram illustrating the structure of the color-simulating apparatus according to one embodiment of this invention.

Referring to FIG. 1, according to the first embodiment of the present invention, the color-simulating apparatus comprises: a light source device 10, a demodulation device 14 and a light-emitting device 16.

Figure 4:
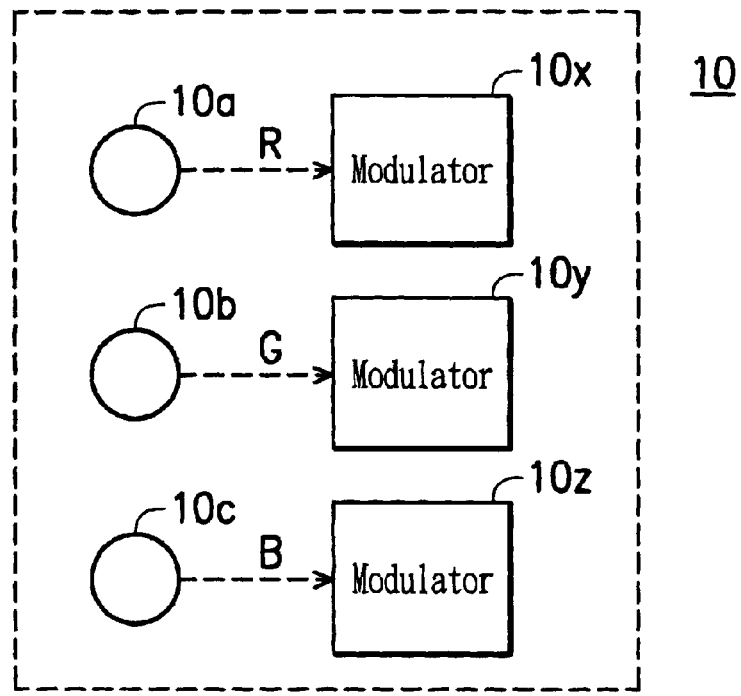
FIG. 4 is a diagram illustrating the structure of the light source device used in the color-simulating apparatus of FIG. 1.

Referring to FIG. 4, the light source device 10 includes three-primary-colored light sources 10a~10c for providing lights of three primary colors, and modulators 10x~10z for modulating the lights of three primary colors, respectively.

Figure 5:
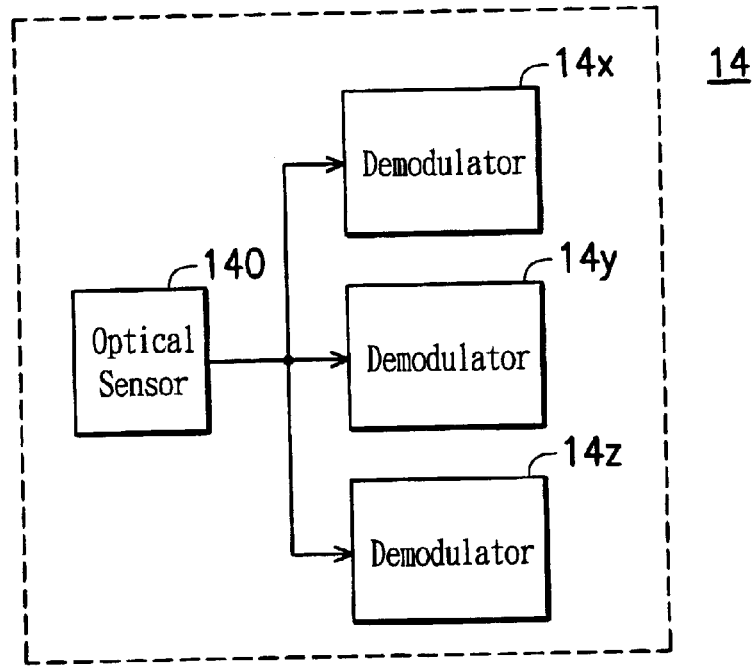
FIG. 5 is a diagram illustrating the structure of the demodulation device used in the color-simulating apparatus of FIG. 1.

The modulated lights of three primary colors produced by the light source device 10 is reflected by the article 12 and is then received by the demodulation device 14. Referring to FIG. 5, the demodulation device 14 includes an optical sensor 140 and demodulators 14x~14z.

Corresponding to the modulation way of the modulators 10x~10z, the demodulation device 14 demodulates the modulated signals. For instance, if the modulators 10x~10z modulate the lights of three primary colors with three different frequencies $f_1$, $f_2$ and $f_3$, then the demodulation device 14 has to demodulate the modulated signals corresponding to the three frequencies $f_1$, $f_2$ and $f_3$.

The reflectivity of the article's surface is different for different colored lights. Therefore the lights of three primary colors has different light intensities after being reflected by the article. The intensity signals of the three-primary-colored lights can be obtained by using the demodulation device 14 to demodulate the signals of the reflected light.

The light-emitting device 16 includes light-emitting elements of three colors, such as light-emitting diode or laser diode. The driving circuit of the light-emitting device receives the intensity signals output from the demodulation device 14 and then drives the light-emitting elements of three colors to emit a colored light to simulate the color of the article 12.

Figure 2:
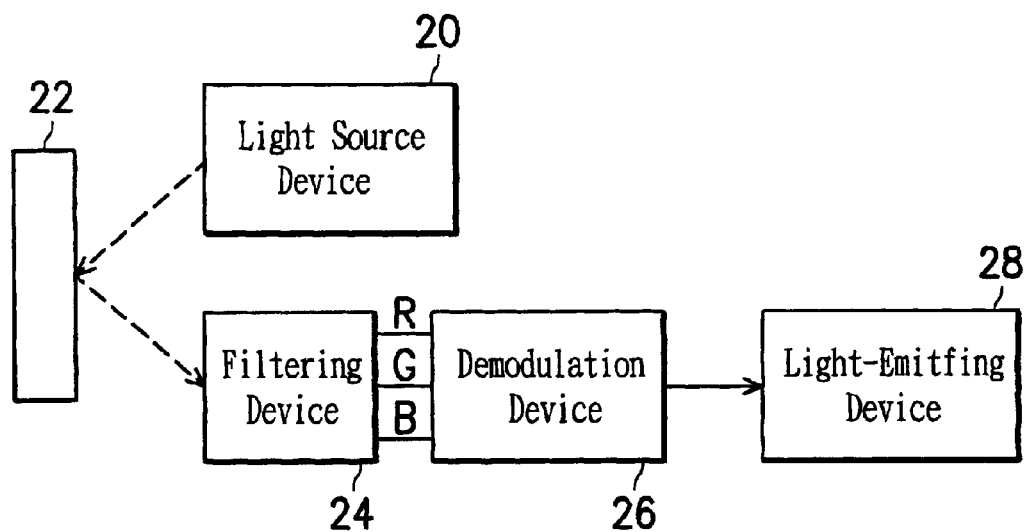
FIG. 2 is a diagram illustrating the structure of the color-simulating apparatus according to another embodiment of this invention.

Referring to FIG. 2, according to the second embodiment of the present invention, the color-simulating apparatus comprises: a light source device 20, a filtering device 24, a demodulation device 26 and a light-emitting device 28.

The light source device 20 includes a white light source for emitting a white light and a modulator for modulating the white light.

The modulated white light produced by the light source device 20 is projected to and is then reflected by the surface of the article 22.

The reflected white light is directed toward the filtering device 24, which includes filters of three primary colors for filtering out the lights of three primary colors from the white light.

The lights of three primary colors obtained through the filtering device 24 are received by the demodulation device 26.

Figure 6:
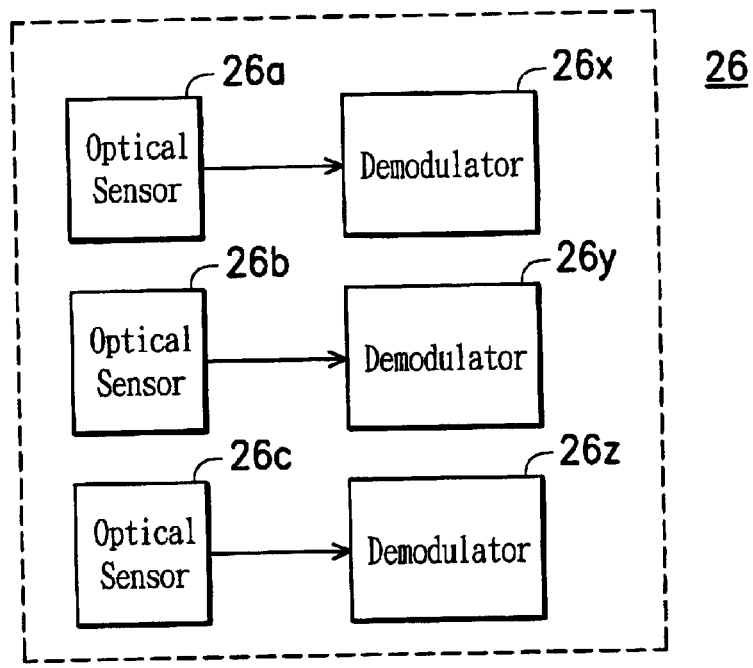
FIG. 6 is a diagram illustrating the structure of the demodulation device used in the color-simulating apparatus of FIG. 2.

Referring to FIG. 6, the demodulation device 26 includes optical sensors 26a~26c and demodulators 26x~26z. The optical sensors 26a~26c respectively receive the lights of three primary colors and convert the optical signals of the lights to electrical signals. The demodulators 26x~26z respectively demodulate the electrical signals to obtain the intensity signals of the three-primary-colored lights.

In this embodiment, the modulation/demodulation of the lights is adopted to prevent the signals from the interference of noise signals. Regarding the modulation/demodulation way, for instance, the white light can be modulated with a certain frequency f. The demodulation device 26 demodulates the modulated lights corresponding to the frequency f.

Figure 3:
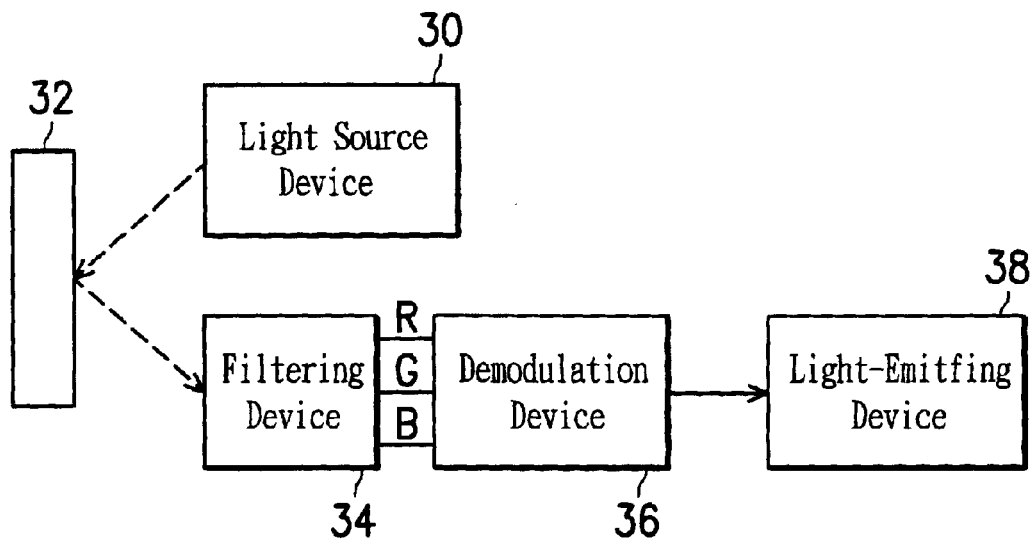
FIG. 3 is a diagram illustrating the structure of the color-simulating apparatus according to the other embodiment of this invention.

Referring to FIG. 3, according to the third embodiment of this invention, the color-simulating apparatus comprises: a light source device 30, a filtering device 34, a demodulation device 36 and a light-emitting device 38.

The light source device 30 is the same as the light source device 10 of the first embodiment. The modulated lights of three primary colors produced by the light source device 30 are projected to and then reflected by the surface of the article 32.

The reflected three-primary-colored lights are directed toward the filtering device 34, which includes filters of three primary colors for respectively passing the lights of three primary colors.

Figure 7:
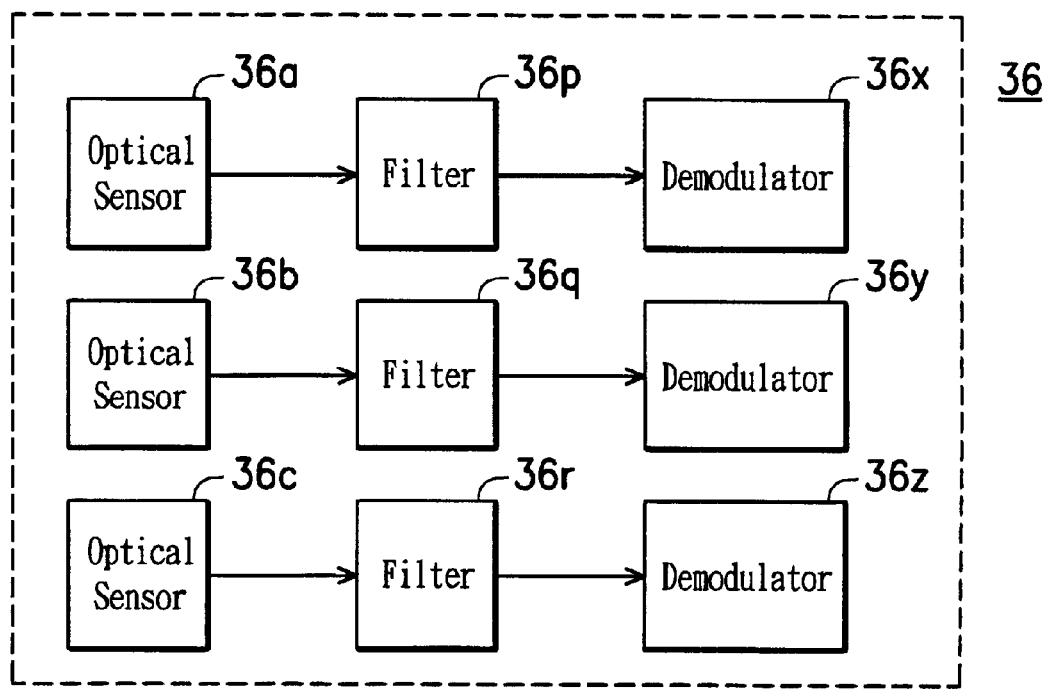
FIG. 7 is a diagram illustrating the structure of the demodulation device used in the color-simulating apparatus of FIG. 3.

Referring to FIG. 7, the demodulation device 36 includes optical sensors 36a~36c, filters 36p~36r and demodulators 36x~36z. The filters 36p~36r are used to further purify the lights of three primary colors obtained through the filtering device 34, respectively. The optical sensors 36a~36c respectively receive the lights of three primary colors and then convert the optical signals of the lights to electrical signals. After filtering out some noise signals by the filters 36p~36r, the demodulators 36x~36z respectively demodulate the electrical signals to obtain the intensity signals of the three-primary-colored lights.

The filters 36p~36r can be band-pass filters for passing the signals having a certain frequency range. Since the light source device 30 modulates the lights of three primary colors with different frequencies, the filters 36p~36r can be used to pass different colored lights of three primary colors, respectively.

The color-simulating apparatus of the above embodiments can emit a colored light corresponding to the color of the article. In practice, a light guiding apparatus can be used to direct the colored light toward a certain position. For example, the color-simulating apparatus can be applied to a cup. A light-guiding layer is formed on the outer surface of the cup. Light diffuser is doped into the light-guiding layer. Thus, when the cup is placed on a table, the color-simulating apparatus can emit a colored light corresponding to the color of the table. The colored light is transmitted to the whole surface of the cup through the light-guiding layer, and is uniformly emitted from the surface of the cup due to the affect of the light diffuser. This method can be applied to various articles to change the color of an article.

Besides, the colored light emitted by the color-simulating device can directly illuminate the surface of an article. The article can present various colors when the color-simulating apparatus is placed on an environment having various colors.

Finally, while the invention has been described by way of example and in terms of the preferred embodiment, it is to be understood that the invention is not limited to the disclosed embodiments. On the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A color-simulating apparatus comprising:
   a light source device for providing modulated lights of three primary colors, which are projected on an article and reflected by the article;
   a demodulation device for receiving the lights reflected by the article and demodulating the lights to output signals representing the intensity of the three primary colored lights; and
   a light-emitting device for generating a colored light according to the intensity signals output from the demodulation device.

2. The color-simulating apparatus as claimed in claim 1, wherein the light source device comprises:
   a three-primary-colored light source for providing three primary colored lights; and
   a modulation device for modulating the three primary colored lights.

3. The color-simulating apparatus as claimed in claim 1, wherein the demodulation device comprises:
   an optical sensor for receiving the light reflected by the article and converting optical signals to electrical signals; and
   a demodulator for demodulating the electrical signals to respectively output intensity signals of the three-primary-colored lights.

4. The color-simulating apparatus as claimed in claim 1, wherein the light-emitting device comprises at least one three-primary-colored light source.

5. A color-simulating apparatus comprising:
   a light source device for providing modulated light, which is projected on an article and reflected by the article;
   a filtering device for separating the light into lights of three primary colors;
   a demodulation device for receiving the three-primary-colored lights and demodulating the lights to output signals representing the intensity of the three primary colored lights; and
   a light-emitting device for generating a colored light according to the intensity signals of the three-primary-colored lights output from the demodulation device.

6. The color-simulating apparatus as claimed in claim 5, wherein the light source device comprises:
   a white light source for providing a white light; and
   a modulation device for modulating the white light.

7. The color-simulating apparatus as claimed in claim 5, wherein the filtering device includes filters of three primary colors for filtering out lights of three primary colors from the white light.

8. The color-simulating apparatus as claimed in claim 5, wherein the demodulation device comprises:
   an optical sensor for receiving the three-primary-colored lights and converting optical signals to electrical signals; and
   a demodulator for respectively demodulating the electrical signals to obtain intensity signals of the three-primary-colored lights.

9. The color-simulating apparatus as claimed in claim 5, wherein the light-emitting device comprises at least one three-primary-colored light source.

10. The color-simulating apparatus as claimed in claim 5, wherein the light source device comprises:
    a three-primary-colored light source for providing three-primary-colored lights; and
    a modulation device for modulating the three-primary-colored lights.

11. The color-simulating apparatus as claimed in claim 5, wherein the demodulation device comprises:
    optical sensors for receiving the three-primary-colored lights and converting optical signals to electrical signals;
    filters for respectively receiving the electrical signals output from the optical sensors and filtering out noises of the electrical signals; and
    demodulators for respectively demodulating the filtered electrical signals to obtain intensity signals of the three-primary-colored lights.

* * * * *